(12) United States Patent
Lihl et al.

(10) Patent No.: US 7,232,546 B2
(45) Date of Patent: *Jun. 19, 2007

(54) APPARATUS FOR TISSUE PROCESSING FOR THE TISSUE EMBEDDING

(75) Inventors: Reinhard Lihl, Vienna (AT); Guenther Bock, Vienna (AT); Ian Lamswood, Vienna (AT); Michael Zimmermann, Leopoldsdorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 789 days.

This patent is subject to a terminal disclaimer.

(21) Appl. No.: 10/100,850

(22) Filed: Mar. 18, 2002

(65) Prior Publication Data

US 2002/0150510 A1 Oct. 17, 2002

(30) Foreign Application Priority Data

Mar. 22, 2001 (EP) ................................. 01107116

(51) Int. Cl.
*G01N 25/00* (2006.01)
(52) U.S. Cl. ......................... 422/64; 422/62; 436/43; 436/46; 436/50
(58) Field of Classification Search .................. 436/43, 436/46, 50, 63, 174–177; 422/62, 64
See application file for complete search history.

(56) References Cited

U.S. PATENT DOCUMENTS

| 3,807,353 | A | * | 4/1974 | Kobernick | ................... 118/702 |
| 4,204,917 | A | * | 5/1980 | Yamamoto et al. | ....... 205/781.5 |
| 4,530,304 | A | * | 7/1985 | Gardos | ......................... 118/66 |
| 4,688,517 | A | | 8/1987 | Hollman | |
| 5,419,871 | A | * | 5/1995 | Muszak et al. | ................ 422/63 |
| 5,582,796 | A | * | 12/1996 | Carey et al. | ................... 422/65 |
| 6,594,537 | B1 | * | 7/2003 | Bernstein et al. | ........... 700/100 |
| 2003/0031602 | A1 | * | 2/2003 | Weselak et al. | .............. 422/104 |

OTHER PUBLICATIONS

"Leica TP 1020, Reliable technology, maximum specimen safety." Leica Brochure 1996.

* cited by examiner

*Primary Examiner*—Lyle A. Alexander
(74) *Attorney, Agent, or Firm*—Simpson & Simpson, PLLC

(57) ABSTRACT

An apparatus (1) for tissue preparation for the tissue embedding, having a transport plate (15) that is surrounded by a housing (5). The housing defines an inner upper side (8a), a heating and cooling device (3), that is provided on the inner upper side (8a) of the housing (5) and a mechanic module (24) for turning the transport plate (15) and for raising and lowering the transport plate (15). The mechanic module (24) comprises a first motor (42) exclusively for turning the transport plate (15) around an axle (18) and a second motor (44) exclusively for raising and lowering the transport plate (15) in the direction of the axle (18).

9 Claims, 5 Drawing Sheets

APPARATUS FOR TISSUE PROCESSING FOR THE TISSUE EMBEDDING

CROSS REFERENCE TO RELATED APPLICATIONS

This invention claims priority of the European patent application 01 107 116.4, filed Mar. 22, 2001, which is incorporated by reference herein.

FIELD OF THE INVENTION

The invention concerns an apparatus for tissue processing for tissue embedding.

BACKGROUND OF THE INVENTION

The U.S. Pat. No. 4,688,517 discloses an apparatus for processing tissue samples. On a rotatable table a plurality of processing containers is provided for the sample processing. The table is rotatable so that the processing containers can be transported to a processing station at which the tissue samples are successively immersed in different processing liquids. For a suitable tempering of the actually used processing liquids a heating and cooling device is permanently mounted to the housing of the apparatus. The table is not only rotatable but also raisable and lowerable in the direction of the axle. The rotation, the raising and the lowering are executed with a single motor, which requires a complicated transmission.

A further apparatus for tissue preparation for the tissue embedding is disclosed with the LEICA TP 1020™. The processing liquids are supplied in processing containers which are arranged in a circle. The samples which are to be processed, are stored in suitable sample containers arranged in the cover of the device. The samples are transferred by raising and rotating the cover from one processing bath into the next. The device cannot handle two processing containers of different size.

SUMMARY OF THE INVENTION

It is an object of the invention to provide an apparatus for tissue preparation for the tissue embedding with which the handling is simplified in the transfer processes become simply controllable.

The above object is solved by an apparatus which comprises:
- a transport plate for holding a plurality of processing containers;
- a housing, which defines an inner upper side and wherein the housing surrounds the transport plate;
- a heating and cooling device provided on the inner upper side of the housing; and
- a mechanic module for rotating the transport plate and for raising and lowering the transport plate, wherein the mechanic module has a first motor exclusively for rotating the transport plate around an axle and a second motor exclusively for raising and lowering the transport plate in the direction of the axle.

An advantage of the invention is that by the use of a first motor for the rotation of the transport plate around the axle and a second motor for the raising and lowering of the transport plate, a complex transmission is not necessary. In addition, the allocation of a movement process in each case to one engine a more exact in more variable control is possible. The rotating motion of the first motor is transformed with a transmission means into a rotation about the axle. Likewise the rotating motion of the second motor is transformed by a transmission means into a raising and a lowering of the transport plate. The transmission means comprises at least one toothed belt. The usable toothed belts are designed in such a manner that an exact and slip-free transfer of the rotating motion of the motor is enabled.

The device according to the invention for tissue preparation for the tissue embedding possesses besides the transport plate, surrounded by a housing, a heating and cooling device which is provided on the inner upper side. A mechanics module for the rotation of the transport plate and for the raising and lowering the transport plate encompasses all mechanical means necessary. Furthermore, a free space is formed in the housing in which the transport plate is rotatably mounted around the axle. The transport plate is composed of a dome and an edge element, whereby the edge element has a plurality of cut outs formed for accommodation of a plurality of processing containers. The apparatus permits likewise that processing containers with different volumes in diameters can be set on the transport plate.

A heating and cooling device is intended which is easily removable, so that the user can switch in a simple manner between processing containers of different size. This is of advantage if large tissue pieces for the tissue embedding must be processed. In addition, the possibility to pivot the heating and cooling device eases the replacement of the transport plate substantially. The heating and cooling device will thus be lifted away from the free space in the housing. It is not necessary that some processing containers must be removed from the transport plate in order to enable the replacement. The replacement of the heating and cooling device can be particularly easily executed. For this the pins are to be removed from the hinges and subsequently the entire heating and cooling device can be removed. A coding is transmitted to the control unit in the housing which then controls the rotating and the lifting motion of the transport plate accordingly. With the different heating and cooling devices the accommodations for the processing containers are of various sizes and in each case permanently connected to the power supply for the heating and cooling device. In one embodiment of the invention the accommodation for the processing containers is designed in such a way that a first and a second chamber for the processing containers are provided, whereby the second chamber has a cover. The first chamber serves for tempering the processing liquid in the processing container and for immersing the tissue sample into the processing container. The second chamber can be used for preheating the processing liquid in the processing container. The cover prevents an unnecessary evaporation of the processing liquid.

BRIEF DESCRIPTION OF THE DRAWINGS

In the drawing the invention is schematically shown and described on the basis of the figures below. The figures show in.

DETAILED DESCRIPTION OF THE INVENTION

Figure 1:
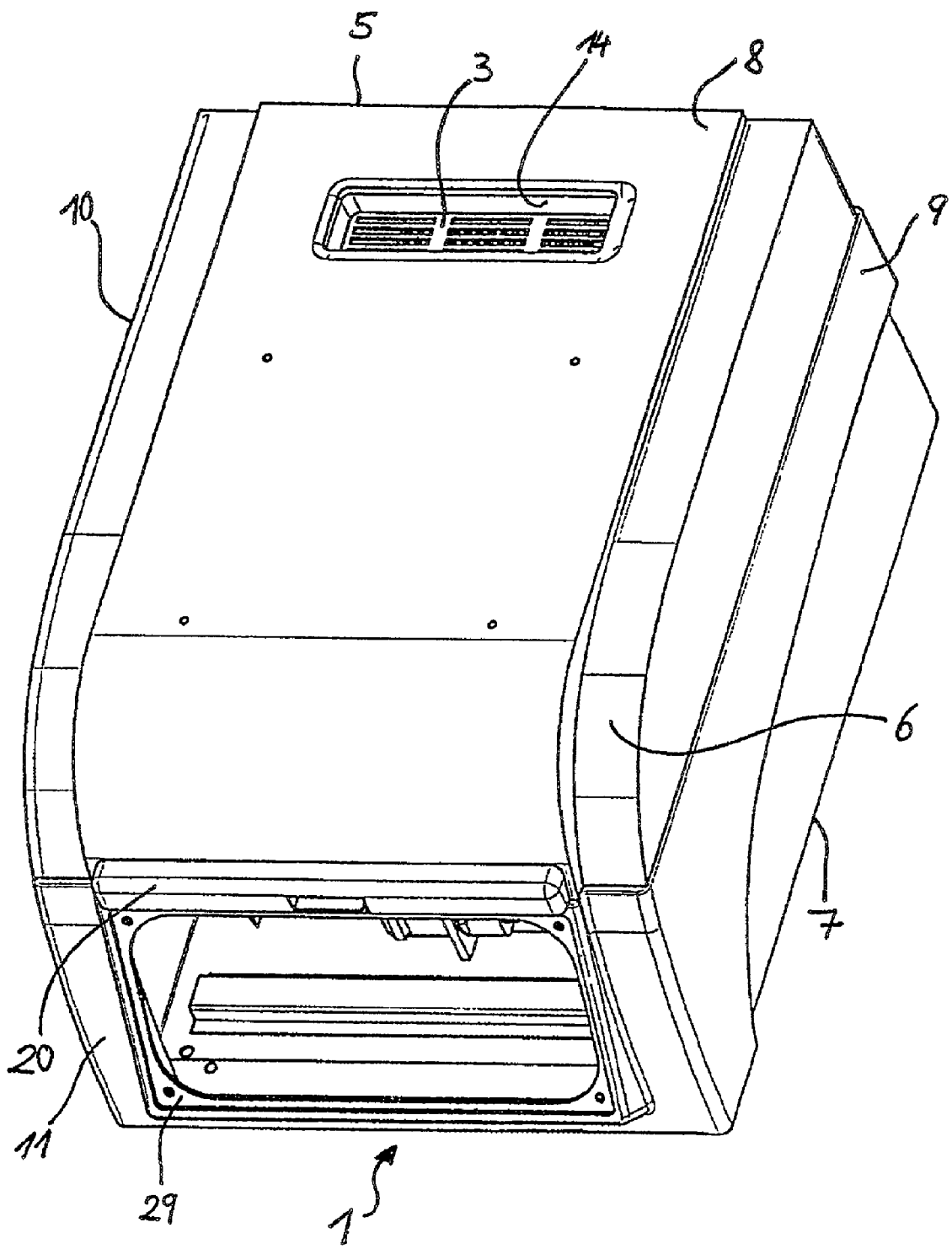
FIG. 1 a perspective view of the apparatus for tissue preparation for tissue embedding.

The apparatus 1 or tissue preparation for the tissue embedding is shown in FIG. 1 in a perspective view. The apparatus 1 for tissue preparation for the tissue embedding consists of a housing 5, which essentially encloses the mechanical and electronic parts (not represented in FIG. 1) of the apparatus 1. The housing 5 comprises an under side 7, an upper side 8, a right and a left side wall 9 and 10 and a front and a back side 11 and 12. The upper side 8 of the housing 5 is formed as a cover 6. The cover 6 is rounded off to the front side 11. The cover 6 can be manufactured out of a transparent plastic part. In the cover 6 a cut out 14 is formed, which allows an air supply of the ambient air to a heating and cooling device 3 provided in the housing 5. The connection of the heating and cooling device 3 to the ambient air is necessary in order to obtain a cooling and to avoid an undesired heating up the inside of the housing 5. At the front side 11 of the housing 5 an approximately rectangular recess 29 is formed into which a control element (not shown) for the user can be placed. From the control element the user is able to recall or design various processing programs. At the cover 6 a handle is formed which facilitates the opening and closing of the cover 6.

Figure 2:
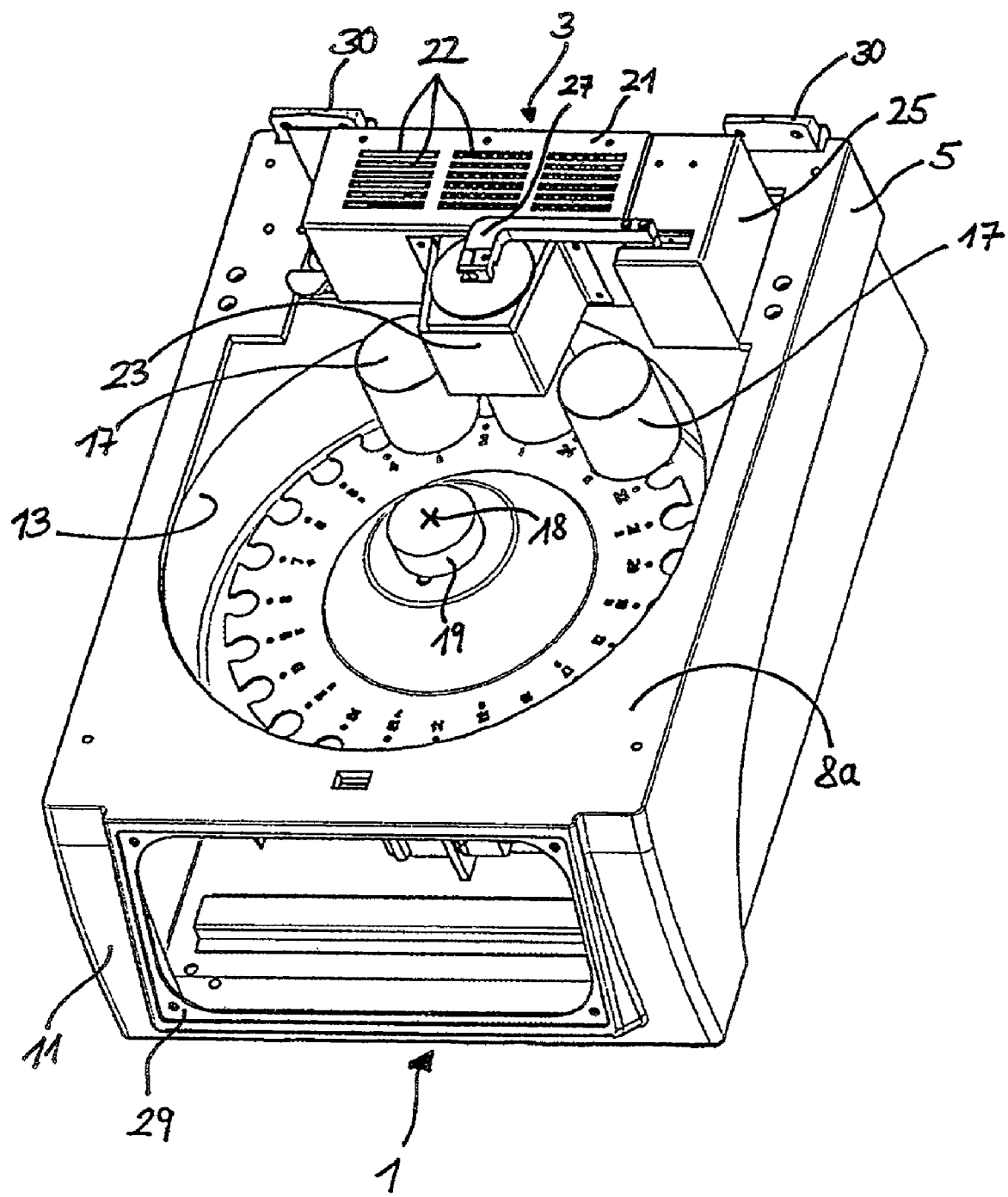
FIG. 2 a perspective view of the apparatus for tissue preparation for the tissue embedding without the protective cover.

FIG. 2 depicts a perspective view of the apparatus 1 for tissue preparation for the tissue embedding wherein the cover 6 is removed. For the sake of simplicity the same reference numerals are used for the same features. The housing 5 has an inner upper side 8a, in which a free space 13 is provided by which the access to the inside of the apparatus 1 is enabled. By the free space 13 access to the transport plate 15, arranged inside the housing 5, is possible. The transport plate 15 is configured in this embodiment in a circular shaped manner and possesses at its edge a plurality of cut outs 16, which serve for the accommodation of processing containers 17. In this embodiment processing containers 17 are shown which have a large volume for the processing liquid. The transport plate 15 is freely rotatable around an axle 18 and can be raised and lowered additionally in the direction of the axle 18. The transport plate 15 is secured by means of a securing element 19. With the housing 5 the heating and cooling device 3 is connected. The heating and cooling device 3 consists of a power supply 21, which is provided with several vent openings 22, for venting off the produced heat. To the power supply 21 a reception 23 for the processing containers 17 is attached, which is arranged in such a manner that it projects at least partly into the area of the free space 13. As mentioned already above, the transport plate 15 can be raised and lowered in the direction of the axle 18. In the raised status at least one processing container 17 is in the reception 23 and can be kept at a temperature in an appropriate way. Different liquids are in the processing containers 17, the different liquids are necessary for the processing of the tissue samples. Beside the heating and cooling device 3 a mechanic 25 is provided to which an arm 27 is connected. At the arm 27 a tissue sample (not represented) is attached, which is submitted to an appropriate sample processing program. The arm 27 can move up and down, whereby the tissue sample is dipped into the liquid which is in the processing container 17 being in the reception 23 at the moment. With the housing 5 hinge elements 30 are connected with which the cover 6 can be pivoted.

Figure 3:
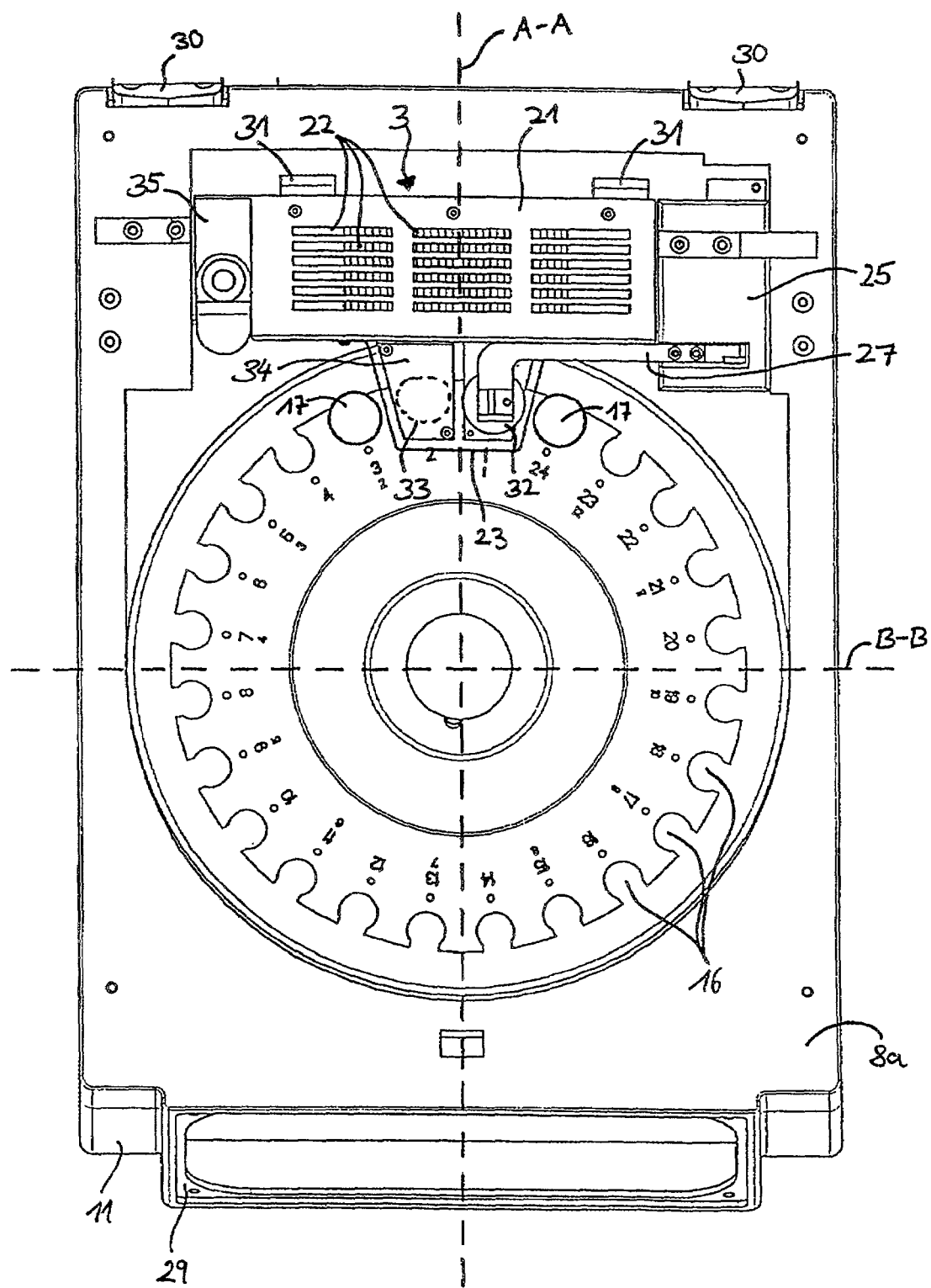
FIG. 3 a plan view of a second embodiment of the apparatus for tissue preparation for the tissue embedding.

FIG. 3 shows a plan view of the apparatus 1 for tissue processing for the tissue embedding. The further embodiment covers an reception 23, into which at least two processing containers 17 can be inserted at the same time. The heating and cooling device 3 consists of the power supply 21 and the reception 23 for the processing containers 17. At least one hinge 31 is provided at the side of the power supply 21 which is opposite to the reception 23 for the processing containers 17. In the embodiment shown here two hinges 31 are provided. With the hinges 31 the entire heating and cooling device 3 can be pivoted away from the upper side 8 of the housing 5. Thus the area above the free space 13 becomes free from obstacles and the transport plate 15 can be taken out of the housing 5 be in a simple manner. In addition, the hinges 31 can be loosened in a simple manner in order to thus quickly exchange the heating and cooling device 3 against another embodiment of the heating and cooling device 3 (see FIG. 3). The reception 23 for the processing containers 17 is provided opposite to the side of the power supply 21 at which the hinges 31 are mounted. In the embodiment shown in FIG. 3, the reception 23 is divided into first and a second chamber 32 and 33. The first chamber 32 is cylindrical and open at the top and on the bottom. The processing container 17 can be introduced from the bottom and from above the arm 27 with the tissue sample can dip into the processing liquid. The second chamber 33 (represented in broken lines, since not to see) is of cylindrical form as well and closed at the tope with a plate 34. The second chamber 33 (shown with broken lines) serves for preheating or pre-cooling the processing liquids in a processing container 17. The plate 34 thus prevents an evaporation of the processing liquid. On the transport plates 15 numbers are provided opposite to the cutouts 16. Those numbers, which face the cut out 16 directly, represent for the size of processing containers 17 as shown in FIG. 3. If the larger processing containers 17b are used, which possess for instance a five times larger volume, those numbers on the transport plate 15 are used for the numbering, which are further distant from the cut out 16. As already shown in FIG. 2, the numbering nearest to the cut out 16 is covered, when the large processing containers 17b are used.

As well, a latch 35 is fastened to the power supply 21, the latch 35 connects the heating and cooling device 3 with the housing 5 in the working position. In addition, an interlock (not represented) is intended at the housing 5, which serves for safe positioning of the heating and cooling device 3 to the housing 5. This connection which can be made easily is important on the one hand, in order to change heating and cooling device 3 and on the other hand to achieve a fix and unchangeable position of the heating and cooling device 3 with respect to the housing 5. The unchangeable and fixed position is necessary in order to ensure that the processing containers 17 can be inserted into the first and second chamber 32 and 33 without cant.

Figure 4:
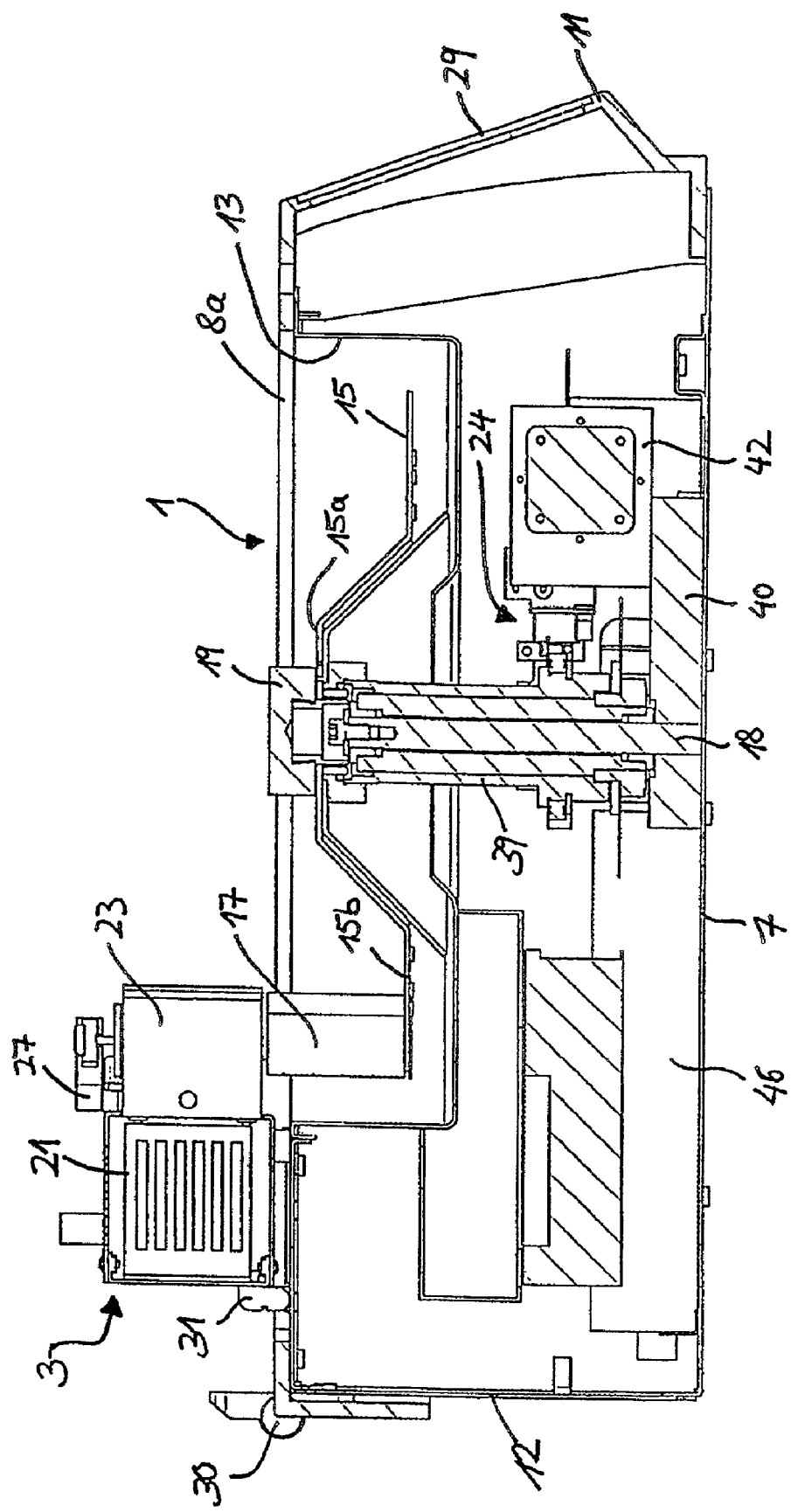
FIG. 4 a cross sectional view of the apparatus taken along line A-A of FIG. 3, whereby the mechanism to move the transport plate is shown as well.

In FIG. 4 the apparatus 1 for tissue processing for the tissue embedding is shown along the cut along the line A-A of FIG. 3. The transport plate 15 is positioned in the free space 13. The transport plate 15 comprises an elevated central dome 15a at which a surrounding, flat edge element 15b is attached. The edge element 15b carries the processing containers 17. In the centre of the dome 15a the axle 18 is located which is surrounded by an axially movable sheath 39. The transport plate 15 is connected to the securing element 19 with the axle 18. Before the transport plate 15 is exchanged, the securing element 19 must be loosened. In the interior of the housing 5 a mechanic module 24 is provided which serves for the execution of the different movement patterns of the transport plate 15. The mechanic module 24 is provided on the under side 7 of the housing 5 and consists of a base plate 40 on which the axle 18 is mounted. Furthermore, on the base plate 40 a first motor 42 and a second motor 44 are mounted (see FIG. 5). The first motor 42 serves to turn the transport plate 15 around the axle 18. The rotation of the first motor 42 can be transferred for example by means of a toothed belt (not shown) to the axle 18. As well, a control electronic 46 is provided at the under side 7 of the housing 5, that controls and regulates the mode of operation of the apparatus 1. On the inner upper side 8*a* of the housing 5, the heating and cooling device 3 is mounted in such a way, that the reception 23 for the processing containers 17 reaches into the area of the free space 13. Thereby, it is important that the processing containers 17 are so positioned underneath the reception 23, that it is introduced into the reception 23 by raising the transport plate 15. When the transport plate 15 raised, the sample is submerged into the processing containers 17 by the arm 27 arranged above the heating and cooling device 3. The heating and cooling device 3 is connected with the inner upper side 8*a* of the housing 5 with at least one hinge 31 in a pivotable manner with apparatus 1. As well, hinge elements 30 are planned on the back side 12 for the opening and closing of the cover 6.

Figure 5:
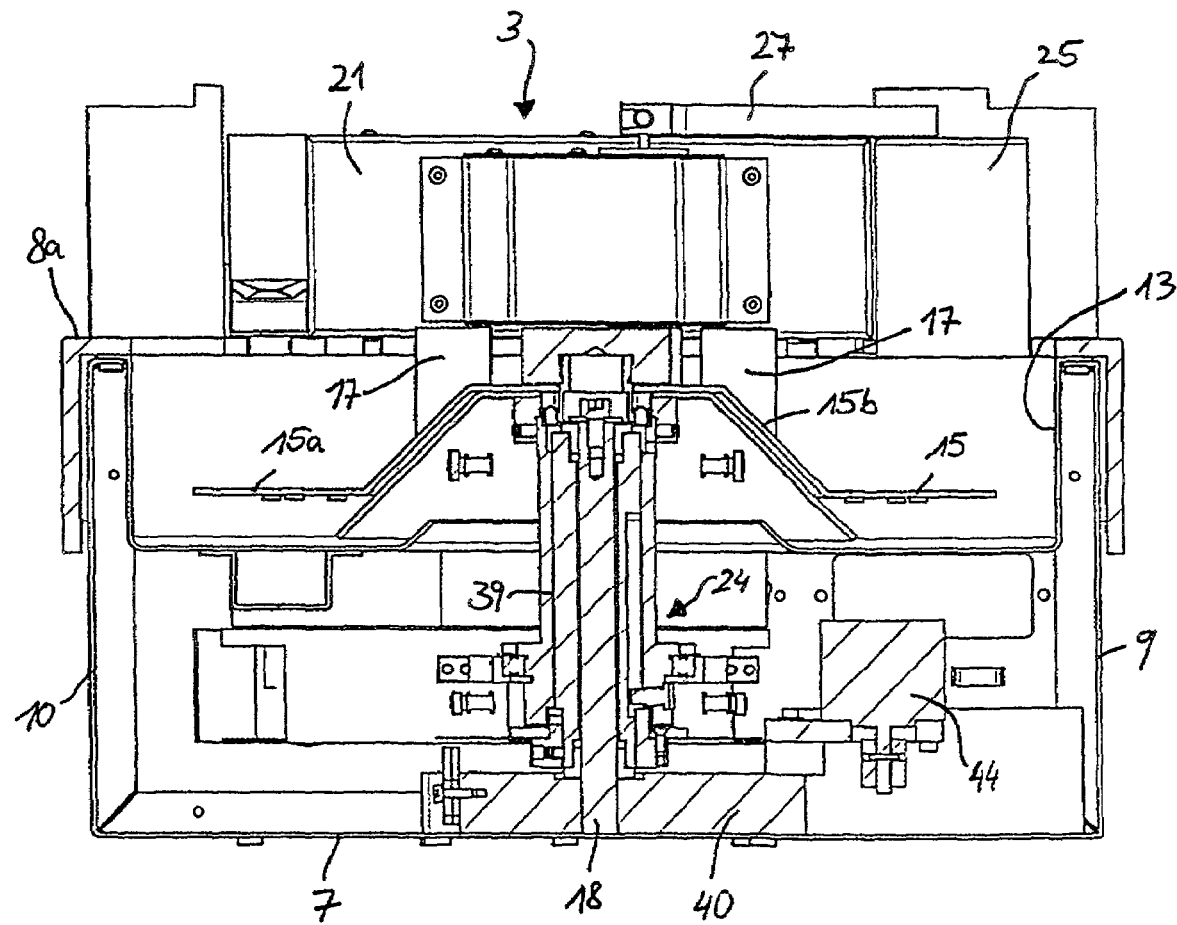
FIG. 5 a cross sectional view of the apparatus taken along line B-B of FIG. 3, whereby the mechanism to move the transport plate can be seen as well.

A view of the apparatus along the cut line B-B, as shown in FIG. 3, is disclosed in FIG. 5. The second motor 44 is mounted also on the base plate 40. The rotation of the second motor 44 is transferred over toothed belts (not shown) to the movable sheath 39. Depending on the direction of rotation of the second motor 44, the transport plate 15 is raised or lowered in the direction of the axle 18. The free space 13 in which the transport plate 15 is placed, extends essentially from the left side wall 10 to the right side wall 9. The power supply 21 and the reception 23 for the heating and cooling device 3 are arranged on the inner upper side 8*a*, so that in the case of a lowered transport plate 15 the processing containers 17, inserted on the transport plate 15, allow a free rotating movement of the transport plate 15 under the reception. The rotating movement of the transport plate 15 around the axle 18 with the first motor 42 is only possible if the transport plate 15 is in the lowered position.

The invention was described with respect to a specific embodiment of the invention. It is however obvious that changes and modifications can be carried out without leaving the scope of protection of the claims below.

PARTS LIST 1 apparatus
3 heating and cooling device
5 housing
6 cover
7 under side
8 upper side
8*a* inner upper side
9 right side wall
10 left side wall
11 front side
12 back side
13 free space
14 cut out
15 transport plate
15*a* dome
15*b* edge element
16 cut out
17*a* small processing container
17*b* large processing container
18 axle
19 securing element
20 handle
21 power supply
22 vent opening
23 reception
24 mechanic module
25 mechanic
27 arm
29 recess
30 hinge element
31 hinge
32 first chamber
33 second chamber
34 plate
35 latch
37 protective cover
39 movable sheath
40 base plate
42 first motor
44 second motor
46 control electronic
A-A line
B-B line

What is claimed is:

1. An apparatus for tissue preparation for the tissue embedding comprises:
    a circular transport plate for holding a plurality of processing containers;
    a housing, which defines an inner upper side and wherein the housing surrounds the transport plate;
    a heating and cooling device provided on the inner upper side of the housing wherein the heating and cooling device is pivotable to one position with respect to the housing of the apparatus, so that the area above the free space becomes free from obstacles and wherein the heating and cooling device is pivotable to another position in the housing so that the heating and cooling device can heat or cool the tissue preparation; and,
    a mechanic module for rotating the circular transport plate and for raising and lowering the circular transport plate, wherein the mechanic module has a first motor exclusively for rotating the circular transport plate around an axle and a second motor exclusively for raising and lowering the circular transport plate in the direction of the axle.

2. The apparatus as defined in claim 1, wherein the housing defines a free space, in which the circular transport plate is arranged rotatably around the axle.

3. The apparatus as defined in claim 1 wherein the circular transport plate is constructed of a dome and an edge element, wherein the edge element has a plurality of cut outs which are designed to receive the plurality of processing containers.

4. The apparatus as defined in claim 2, wherein the heating and cooling device is essentially formed of a power supply and a reception for the processing containers, the heating and cooling device is arranged in such a way at the inner upper side of the housing that the reception reaches into the area of the free space, and that at least one processing container is insertable into the reception by raising the circular transport plate.

5. The apparatus as defined in claim 4, wherein at least one hinge is provided on the heating and cooling device at the side which is opposite to the reception for the processing containers, wherein the hinge allows a pivoting motion of the heating and cooling device in order to enable a separation of the circular transport plate from the housing.

6. The apparatus as defined in claim 1, wherein the first motor shows a rotating motion which is transferred to the axle by a transmission means.

7. The apparatus as defined in claim 6, wherein the transmission means is a toothed belt.

8. The apparatus as defined in claim 1, wherein the second motor shows a rotating motion which is transferred by a transmission means to a movable sheath for raising and lowering the movable sheath in the direction of the axle.

9. The apparatus as defined in claim 8, wherein the transmission means encompasses at least one a tooth belt.

* * * * *